United States Patent
Cinquin et al.

(10) Patent No.: US 10,820,922 B2
(45) Date of Patent: Nov. 3, 2020

(54) DEVICE FOR POSITIONING A SURGICAL TOOL IN THE BODY OF A PATIENT

(75) Inventors: Philippe Cinquin, St Nazaire les Eymes (FR); Juan Carlos Avila Vilchis, Toluca (MX); Adriana Herlinda Vilchis Gonzalez, Toluca (MX); Angel Mariano Cruz Abud, Toluca (MX); Jocelyne Troccaz, Eybens (FR)

(73) Assignees: Universite Joseph Fourier—Grenoble 1, St. Martin D'Heres (FR); Universidad Autonoma Del Estado De Mexico, Toluca (MX)

( * ) Notice: Subject to any disclaimer, the term of this patent is extended or adjusted under 35 U.S.C. 154(b) by 376 days.

(21) Appl. No.: 13/056,235

(22) PCT Filed: Jul. 28, 2009

(86) PCT No.: PCT/EP2009/059767
§ 371 (c)(1),
(2), (4) Date: Jan. 27, 2011

(87) PCT Pub. No.: WO2010/012744
PCT Pub. Date: Feb. 4, 2010

(65) Prior Publication Data
US 2011/0126844 A1 Jun. 2, 2011

(30) Foreign Application Priority Data
Jul. 29, 2008 (FR) ...................................... 08 55189

(51) Int. Cl.
*A61B 17/34* (2006.01)
*A61B 17/00* (2006.01)
*A61B 90/11* (2016.01)

(52) U.S. Cl.
CPC .......... *A61B 17/3403* (2013.01); *A61B 90/11* (2016.02); *A61B 2017/00544* (2013.01); *A61B 2017/3407* (2013.01); *A61B 2017/3409* (2013.01)

(58) Field of Classification Search
CPC .............. A61B 17/3403; A61B 19/201; A61B 2017/00544; A61B 217/3407;
(Continued)

(56) References Cited

U.S. PATENT DOCUMENTS 5,201,742 A * 4/1993 Hasson ................... A61B 90/11
606/1
5,235,900 A * 8/1993 Garceau ................ F15B 15/125
92/120

(Continued)

FOREIGN PATENT DOCUMENTS

FR 2875123 3/2006
WO WO 98/49951 11/1998
(Continued)

OTHER PUBLICATIONS

Takayama, T. et al.; "Detachable-Fingered Hands for Manipulation of Large Internal Organs in Laparoscopic Surgery;" Robotics and Automation, 2007; International Conference on IEEE, PI; Apr. 1, 2007; pp. 244-249, ISBN: 978-1-4244-0601-2; p. 245, col. 1, paragraph 2; figures 1,2; p. 244, col. 1, paragraph 3-col. 2, paragraph 1.

(Continued)

*Primary Examiner* — Kari K Rodriquez
*Assistant Examiner* — Caitlin A Carreiro
(74) *Attorney, Agent, or Firm* — Harness, Dickey & Pierce, PLC

(57) ABSTRACT

A device positions and/or orients in the body of a patient, a surgical tool carried by a tool-holder, including a platform
(Continued)

capable of being placed on the body of the patient, an orientable carrier, at least one part of which is rigidly connected to the tool-holder, means for guiding the orientable carrier rotationally relative to the platform in two directions of a plane parallel to the platform, at least 2 pneumatic actuators which engage with the orientable carrier such that a variation in pressure of at least one of the pneumatic actuators causes the orientable carrier to rotate in the first direction and/or the second direction, in which the pneumatic actuators are volumes that can deform in a predetermined direction as a function of the internal pressure.

20 Claims, 5 Drawing Sheets

(58) Field of Classification Search
CPC . A61B 2017/3409; A61B 90/11; A61B 17/34; A61B 17/00
USPC .................. 128/845; 173/218; 606/108, 130; 600/415, 417, 429, 102
See application file for complete search history.

(56) References Cited

U.S. PATENT DOCUMENTS

| | | | |
|---|---|---|---|
| 5,352,219 | A | 10/1994 | Reddy |
| 5,399,951 | A | 3/1995 | Lavallee et al. |
| 5,529,159 | A | 6/1996 | Troccaz |
| 5,752,972 | A | 5/1998 | Hoogeboom |
| 6,074,408 | A | 6/2000 | Freeman |
| 6,385,475 | B1 | 5/2002 | Cinquin et al. |
| 6,685,698 | B2 | 2/2004 | Morley et al. |
| 6,915,150 | B2 | 7/2005 | Cinquin et al. |
| 6,932,089 | B1 | 8/2005 | Cinquin et al. |
| 7,033,360 | B2 | 4/2006 | Cinquin et al. |
| 7,086,309 | B2 | 8/2006 | Stoianovici et al. |
| 7,150,751 | B2 | 12/2006 | Lechot |
| 7,247,116 | B2 | 7/2007 | Stoianovici et al. |
| 7,752,972 | B1 | 7/2010 | Baker et al. |
| 2002/0082518 | A1 | 6/2002 | Weiss et al. |
| 2003/0055436 | A1 | 3/2003 | Wolfgang et al. |
| 2003/0229338 | A1* | 12/2003 | Irion ............ A61B 90/50 606/1 |
| 2004/0133189 | A1 | 7/2004 | Sakurai |
| 2006/0058640 | A1* | 3/2006 | Cinquin ............ A61B 90/11 600/415 |
| 2006/0100501 | A1 | 5/2006 | Berkelman et al. |
| 2007/0034046 | A1 | 2/2007 | Stoianovici et al. |
| 2009/0118610 | A1 | 7/2009 | Karmarkar et al. |

FOREIGN PATENT DOCUMENTS

| | | |
|---|---|---|
| WO | WO03/094579 | 11/2003 |
| WO | WO 2007/064739 | 6/2007 |
| WO | WO 2010/012748 | 2/2010 |

OTHER PUBLICATIONS

Guthart, G.S. et al.; "The intuitive telesurgery system: Overview and application;" IEEE International Conference on Robotics and Automation—ICRA, pp. 618-621, 2000.
Vilchis Gonzales, A. et al.; "TER: A system for robotic tele-echography, in proceedings of Medical Image Computing and Computer Assisted Intervention (MICCAI);" Lecture notes in Computer Science, Springer Verlag, vol. 2208, pp. 326-334, 2001.
Çavuşoğlu, M. et al.; "Robotics for telesurgery: Second generation Berkeley/UCSF laparoscopic telesurgical workstation and looking towards the future applications;" The Industrial Robot: Special Issueon medical robotics, vol. 30, No. 1, pp. 22-29, 2003.
Damiano, R.J. et al.; "Initial prospective multicenter clinical trial of robotically-assisted coronary artery bypass graphting;" Annals of thoracic surgery, vol. 72, pp. 1263-1269, 2001.
Seibold, U. et al.; "Sensorized and actuated instruments for minimally invasive robotic surgery;" Eurohaptics International Conference, pp. 482-485, 2004.
Taylor, R.H. et al.; "Medical robotics in computer-integrated surgery;" IEEE Transactions on Robotics and Automation, vol. 19, No. 5, pp. 765-781, 2003.
Masamune, K. et al.; "System for robotically assisted percutaneous procedures with computed tomography guidance;" Journal of Computer Aided Surgery, vol. 6, No. 6, pp. 370-383, 2001.
Patriciu, A. et al.; "Robotic kidney and spine percutaneous procedures using a new laser-based CT registration method, in proceedings of Medical Image Computing and Computer Assisted Intervention (MICCAI);" Lecture notes in Computer Science, Springer Verlag, vol. 2208, pp. 249-257, 2001.
Chinzei, K. et al.; "MR compatible surgical assist robot: System integration and preliminary feasibility study, in proceedings of Medical Image Computing and Computer Assisted Intervention (MICCAI);" Lecture notes in Computer Science, Springer Verlag, vol. 1935, pp. 921-930, 2000.
Taillant, E. et al.; "CT and MR compatible light puncture robot : Architectural design and first experiments, in proceedings of Medical Image Computing and Computer Assisted Intervention (MICCAI);" Lecture notes in Computer Science, Springer Verlag, vol. 3216, pp. 145-152, 2004.
Berkelman, P. et al.; "Design, control and testing of a novel compact laparoscopic endoscope manipulator;" Journal of Systems and Control Engineering, vol. 27, No. 14, pp. 329-341, 2003.
Hata, N. et al.; "Needle guiding robot with five-bar linkage for MR-guided thermotherapy of liver tumor, in proceedings of Medical Image Computing and Computer Assisted Intervention (MICCAI);" Lecture notes in Computer Science, Springer Verlag, vol. 3217, pp. 161-168, 2004.
Koseki, Y. et al.; "Precise evaluation of positioning repeatability of MR-compatible manipulator inside MRI, in proceedings of Medical Image Computing and Computer Assisted Intervention (MICCAI);" Lecture notes in Computer Science, Springer Verlag, vol. 3217, pp. 192-199, 2004.
Koseki, Y. et al.; "Robotic assist for MR-guided surgery using leverage and parallelepiped mechanism, in proceedings of Medical Image Computing and Computer Assisted Intervention (MICCAI);" Lecture notes in Computer Science, Springer Verlag, vol. 1935, pp. 940-948, 2000.
Nakamura, R. et al.; "Development of a sterilizable MR-compatible manipulator for stereotactic neurosurgery;" International Congress on Computer Assisted Radiology and Surgery, pp. 1019, 1999.
Maurin, B. et al.: "A parallel robotic system with force sensors for percutaneous procedures ubder CT-guidace, in proceedings of Medical Image Computing and Computer Assisted Intervention (MICCAI);" Lecture notes in Computer Science, Springer Verlag, vol. 3217, pp. 176-183, 2004.
Daerden, F. et al.; "Pneumatic artificial muscles: Actuators for robotics and automation;" European Journal of Mechanical and Environmental Engineering, vol. 47, No. 1, pp. 11-21, 2002.
Stoianovici, D. et al.; "A new type of motor: Pneumatic step motor;" IEEE/ASME Transactions on Mechatronics, vol. 12, No. 1, pp. 98-106, 2007.
Patriciu, A. et al.; "Automatic brachytherapy seed placement under MRI guidance;" IEEE Transactions on Biomedical Engineering, vol. 54, No. 8, pp. 1499-1506, 2007.
Gassert, R. et al.; "MRI/fMRI-Compatible robotic system with force feedback for interaction with human motion;" IEEE/ASME Transactions on Mechatronics, vol. 11, No. 2, pp. 216-224, Apr. 2006.
Christoforou, E.G. et al.; "Manipulator for magnetic resonance imaging guided interventions: Design, prototype and feasibility;" IEEE International Conference on Robotics and Automation, pp. 3838-3843, 2006.

(56) References Cited

OTHER PUBLICATIONS

Tsekos, N.V. et al.; "Magnetic resonance-compatible robotics and mechatronics systems for image-guided interventions and rehabilitation: A review study;" Annual Review of Biomedical Engineering, vol. 9, pp. 351-387, 2007.
DiMaio, S.P. et al.; "A system for MRI-guided prostate interventions;" IEEE/RAS-EMBS International Conference on Biomedical Robotics and Mechatronics, pp. 68-73, 2006.
Webster, R.J. III et al.; "Design considerations for robotic needle steering;" IEEE International Conference on Robotics and Automation, pp. 3599-3605, 2005.

* cited by examiner

DEVICE FOR POSITIONING A SURGICAL TOOL IN THE BODY OF A PATIENT

CROSS-REFERENCE TO RELATED APPLICATIONS

This application is a National Phase entry of International Application No. PCT/EP2009/059767, filed on Jul. 28, 2009, which claims priority to French Application Serial No. 0855189, filed on Jul. 29, 2008, both of which are incorporated by reference herein.

FIELD OF THE INVENTION

The present invention relates to a device for positioning a surgical tool in the body of a patient.

BACKGROUND OF THE INVENTION

Scientific interest for the development of automated medical aid systems has considerably increased since the 1990s. Several medical fields have seen the arrival of generic or dedicated systems like in the cases of the Da Vinci™ robot used in laparoscopy but also of systems for tele-operation or for a cardiac application. The advantages of minimally invasive surgery have contributed to the development of particular sensors and actuators. A panorama of the development of medical robots is provided in the article "Medical Robotics in Computer-Integrated Surgery" of Taylor et al, IEEE Transactions on Robotics and Automation, Vol. 19, No. 5, October 2003, where a significant number of robots for different medical specialties is considered.

Generally, tool holder sub-systems (endoscope, laparoscope or needle) have a maximum of 4 degrees of freedom allowing the orientation of the tool, its insertion and its axial rotation. The orientation of the tools outside the body of the patient as well as their insertion are accomplished with actuators. Several kinds of actuators have been considered for robotic systems such as electric motors, ultrasonic motors, piezo-electric motors, harmonic and planetary hydraulic/pneumatic motors or the artificial muscles of McKibben. Artificial muscles use compressed air as a power source and are used in antagonism; therefore their compression rate is low and they bear metal portions which are not desirable in the gantry of tomography or magnetic resonance apparatuses.

In minimally invasive surgery or in puncture procedures, the surgical tools are sometimes orientated or moved manually or with electric actuators which generally are incompatible with the environments of tomography and/or of magnetic resonance, or with other slow actuators. Several automated systems are incompatible with the mentioned environments since they have been built with metal, paramagnetic or diamagnetic materials. These drawbacks are related to mechanical design and to how the systems are actuated.

A lightweight pneumatic robot and compatible with tomography and magnetic resonance environments is presented in the article of E. Taillant et al., "CT and MR Compatible Light Puncture Robot: Architectural Design and First Experiments", Proceedings of Medical Image Computing and Computer Assisted Intervention (MICCAI), Lecture Notes in Computer Science, Springer Verlag, Vol. 3216, pp. 145-152, 2004. This system is adapted to thorax and abdomen puncture under a scanner or magnetic resonance while being interdependent on the body of the patient. With this robot, it is possible to orient the needle holder by means of two rotations: a first rotation of the base of the robot relatively to a platform firmly attached to the body of a patient, of 360° around an axis perpendicular to the body of a patient, and a second rotation of the needle holder, relatively to the base, in a limited angular range.

This orientation device consists of conventional pneumatic actuators, i.e. each comprising a piston sliding in a cylinder fed with compressed air on either side of the piston. Each piston cooperates with a toothed wheel, itself connected to a worm screw, thereby forming a pneumatic step motor. Because of its design, this device therefore only allows positioning of the tool according to a plurality of discrete positions.

This orientation device is also relatively slow, with a frequency of the order of 3 Hz. Moreover, a slipping and adherence (so-called "stick-slip") phenomenon of the piston in the chamber was observed when the piston is motionless, leading to a sudden movement upon its setting into motion and to generation of a delay in the response of the actuator. Finally, another drawback of this robot is its non-compliant nature: because of the rigidity of the drive chain, this robot is not able to absorb large forces so that the latter are capable of injuring the patient when the tool is inside his/her body.

One of the objects of the invention is therefore to design a system allowing fast orientation or displacement of a tool holder (endoscope holder, needle holder or trocar), having a minimum size. This system should also allow continuous variation of the positions of the tool holder. Another object of the invention is that such a system may be compatible with tomography and magnetic resonance environments. Another object of the invention is to provide a lightweight system, guaranteeing the safety of the patient in the case of generation of forces capable of injuring him/her.

SUMMARY

According to the invention, a device is proposed for positioning or/and orientation in the body of a patient, comprising:

- a platform capable of being placed on the body of the patient,
- an orientable support, at least one portion of which is rigidly bound to the tool holder,
- means for guiding in rotation the orientable support relatively to the platform in two directions of a plane parallel to the platform,
- at least two pneumatic actuators cooperating with said orientable support so that a change in pressure of at least one of the pneumatic actuators generates a rotation of the orientable support in the first direction and/or the second direction, wherein said pneumatic actuators are deformable volumes in a direction determined according to the internal pressure, each having a face firmly attached to the platform or guiding means and a face firmly attached to the orientable support, so that a change in the internal pressure causes displacement of the face firmly attached to the orientable support.

According to a first embodiment of the invention, the pneumatic actuators are four in number, the orientable support comprises two pairs of plates, both plates of each pair being parallel to each other and orthogonal to the plates of the other pair, and the pneumatic actuators are laid out as antagonistic pairs so that the internal pressure of an actuator firmly attached to a plate of the orientable support varies in the direction opposite to the internal pressure of the actuator firmly attached to the plate opposite said plate. More advantageously, the guiding means comprise two semi-circular guides positioned longitudinally in the first direction and a second pair of plates in the orientable support has means for sliding along said guides. Said semicircular guides are further mobile in rotation around the first direction and firmly attached to the second pair of plates of the orientable support.

According to a second embodiment of the invention, the pneumatic actuators are three in number and the orientable support is a prism with a triangular base, so that each of the actuators is firmly attached to one of the three side faces of the orientable support. Moreover, the tool holder advantageously comprises means for guiding the tool in translation, in a direction parallel to the axis of the tool holder, said means for guiding the tool cooperating with deformable pneumatic actuators in a determined direction depending on the internal pressure, so that a change in pressure of at least one of said pneumatic actuators causes translation of the tool.

If the translation axis of the tool coincides with the axis of the tool holder, said pneumatic actuators are preferably toroidal cylinders, so that the tool slides inside the toruses. If the translation axis of the tool is distinct from the axis of the tool holder, said pneumatic actuators are cylinders.

The device further comprises means for connecting the platform to the arm of a surgical aid robot; said means comprise at least one passive rotoid joint. More advantageously, the platform, the orientable support, the pneumatic actuators and the means for guiding in rotation the orientable support are in non-metal and non-magnetic materials, so that said device is capable of being used in tomography and/or magnetic resonance.

According to another aspect, the invention relates to a tool holder adapted so as to be used in the device which has just been described. Said tool holder comprises means for driving the tool into translation along an axis, a piston rigidly bound to the tool, slidably mobile in a casing along a longitudinal direction parallel to said axis. Said means advantageously comprise two pneumatic actuators located in the casing on either side of the piston, deformable in a direction determined according to the internal pressure, and cooperating with the piston so that a change in pressure in at least one of the actuators generates sliding of the piston along said direction.

In a particular embodiment of the tool holder, in which the translation axis of the tool and the sliding direction of the piston coincide, the pneumatic actuators are toroidal cylinders, the inner diameter of which is greater than the diameter of the tool. According to an alternative, the translation axis of the tool and the sliding direction of the piston are distinct and the casing has a longitudinal slot for sliding a member connecting the piston and the tool.

SHORT DESCRIPTION OF THE DRAWINGS

Other features and advantages of the invention will become apparent from the detailed description which follows, with reference to the appended drawings wherein.

DETAILED DESCRIPTION OF THE INVENTION

By tool in this text is meant any device which may be used during a surgical operation: it may thereby be a surgical instrument (such as a needle for example) or else a medical imaging system, such as an endoscope or a laparoscope. By tool holder in this text is meant a device bearing the surgical instrument which will be inserted into the body of a patient. Depending on the instrument used, the tool holder may thereby be described as a needle holder, endoscope holder or further a trocar.

Figure 1:
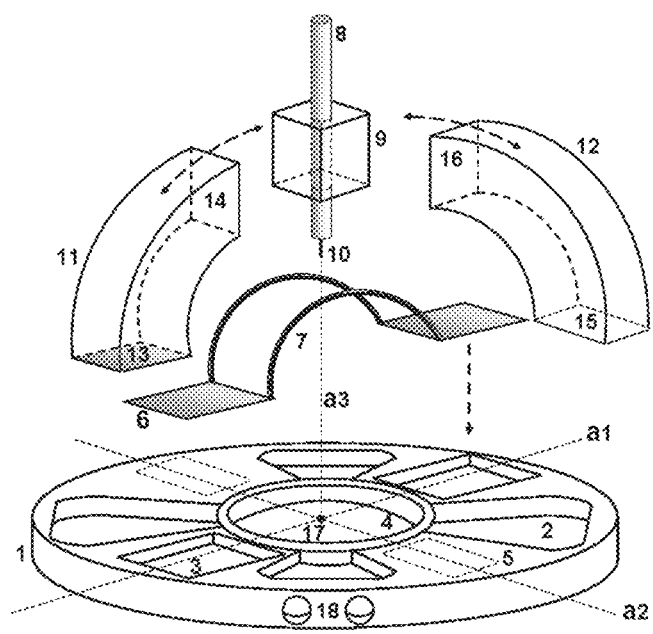
FIG. 1 is an exploded view of a first embodiment of the device according to the invention.

During a surgical operation on a patient, such as a puncture or a laparoscopy, a tool (such as a needle 10 or an endoscope for example) borne by a tool holder 8 as illustrated in FIG. 1 has to be oriented and displaced. The device according to the invention allows the surgeon to orient by means of two rotations, the tool holder 8 along the axes a1 and a2 and to translate the tool along the axis a3. The orientation of the tool holder 8 is controlled via the orientation of the orientable support 9, to which the tool holder 8 is rigidly bound. The tool holder 8 is bound to the orientable support 9 by conventional mechanical means such as screws or clip-fastening means (i.e. by mechanical pressure).

The overview FIG. 1 and the detailed FIGS. 4, 5, 7, and 8 illustrate a preferred but non-limiting embodiment of the invention. According to this preferred embodiment, the device comprises a circular platform 1 comprising four hollow spaces 2 in order to reduce the weight of the system, two hollow spaces 3 for receiving the two rectangular platforms 6 and a circular cavity 4 for defining the working area i.e. the area for introducing the tool into the body of the patient. The platform 1 typically has a diameter of 10 cm.

It is laid on the body of the patient, so that the circular cavity 4 is substantially centered on the area for introducing the tool. In the case of a puncture, the point 17 represents the point of insertion of the needle 10, invariant under the aforementioned rotations. The platform 1 is substantially planar, and the axes a1 and a2 along which the tool holder 8 is orientable are located in a plane parallel to the plane of the platform. The platform 1 may be held by an external mechanical arm (not shown), either rigid or not, of a surgical aid robot, which may be suitably adapted to the contemplated medical applications. The link between the platform and this arm will be described below.

The device moreover comprises two platforms 6 connected through two semicircular guides 7 allowing the angular displacement of the tool holder 8 to be guided by rotation around the axis a2 by means of the orientable support 9. As this will be seen in the description of FIG. 8, the assembly formed by the platform 6 and the semi-circular guides is not rigidly bound to the platform 1 but is rotationally mobile around the axis a1 by means of smooth bolts.

The orientation movements of the tool holder 8 are ensured by pneumatic actuators 11 and 12 which are deformable volumes in a preferential direction depending on the internal pressure. By this is meant that this is the casing defining said volume which deforms, unlike a standard pneumatic actuator in which the cylindrical casing is rigid and the shape of which does not vary. Moreover, the movement produced by a standard pneumatic actuator is always linear while the one produced by pneumatic actuators with a deformable volume follows a preferential direction defined by the shape of the actuator.

The casing of the actuators is for example made in flexible plastic. Here, the actuators appear as portions of toruses, the neutral fiber of which follows approximately a semi-circle. The actuators are capable of elongating or retracting along the neutral fiber.

Two actuators 11 (only one of which is illustrated in FIG. 1) are assembled on the two rectangular platforms 6 by means of the surfaces 13 and on the orientable support 9 by means of the surfaces 14. A change in pressure of one of the actuators 11 therefore allows the orientable support 9 to be tilted in a plane containing the axis a1. Also, two actuators 12 (only one is illustrated in FIG. 1) are assembled on the two rectangular areas 5 of the platform 1 by means of the surfaces 15 and on the orientable support 9 by means of the surfaces 16, thereby allowing the orientable support 9 to be tilted along a plane containing the axis a2.

Figure 2:
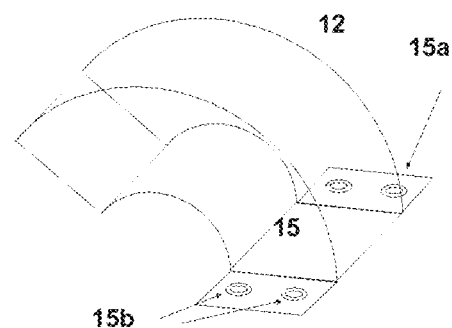
FIG. 2 illustrates a method for attaching an actuator onto the platform.

With reference to FIG. 2, the assembling of each actuator may be carried out by means of plastic screws accommodated in orifices 15b allowing tabs 15a located on the outside of the actuator 12 to be secured in the extension of the surface 15, or else by a mechanical clip-fastening means. Each of the actuators is connected to a compressed air circuit (not shown) provided with means for controlling the pressure in each of them. The handling of the pressures in the different actuators depending on the desired orientation of the tool holder is ensured by an electronic interface (not shown).

Each pair of actuators of the same type work antagonistically, i.e. when the compressed air pressure increases in one of the actuators, that of its antagonist actuator decreases and vice versa. This allows the movements of the orientable support 9 to be balanced. However, it is understood that a single actuator 11 and a single actuator 12 would be sufficient for tilting the orientable support 9. It is therefore understood that these novel actuators give the possibility, unlike conventional pneumatic actuators of the piston-cylinder type, of avoiding the "stick slip" phenomenon, thereby guaranteeing smooth operation of the system.

Figure 3:
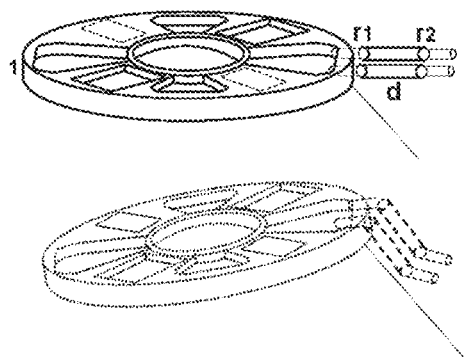
FIG. 3 illustrates two possible orientations of the platform depending on the breathing of the patient.

The two holes 18 shown in the platform 1 of FIG. 1 are used for introducing two cylinders or fingers d associated with two passive rotoid joints r1 and r2 allowing free movement of the system for example produced by the breathing of the patient as illustrated in FIG. 3. Both fingers d are connected to an automated arm allowing translation of the robot in three-dimensional space. Indeed, the device is interdependent on the body of the patient and changes the orientation of the platform 1 depending on the natural movements of the patient.

Figure 4:
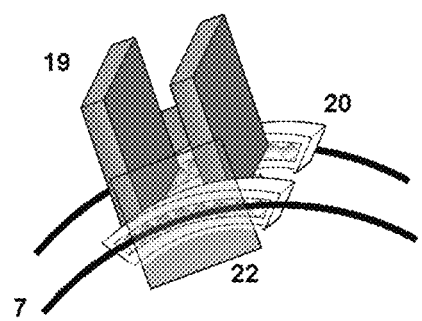
FIG. 4 illustrates the orientable support for the tool holder.

FIG. 3 illustrates two instants when the orientation of the platform 1 has to move freely and naturally, in apnea (upper illustration) and during inspiration (lower illustration). FIG. 4 illustrates in more detail the orientable support 9 which comprises two plates 19 which are used for receiving both contact surfaces 14 of both actuators 11. These plates 19 are rigidly bound to two followers 20 bearing spherical balls in order to reduce the friction between the followers 20 and the internal surfaces of the guides 7.

Both plates 22 are used for receiving both contact surfaces 16 of two actuators 12 and are rigidly bound to the external surfaces of the semi-circular guides 7. The plates 22 are centered relatively to the guide 7, i.e. they are symmetrical with respect to a plane perpendicular to the plane of the platform and comprising the axis a2. It will be noted that as the plates 19 and 22 are not rigidly bound, the tool holder 8 is only rigidly bound to one or two of the plates 19, but not to the plates 22.

Figure 5:
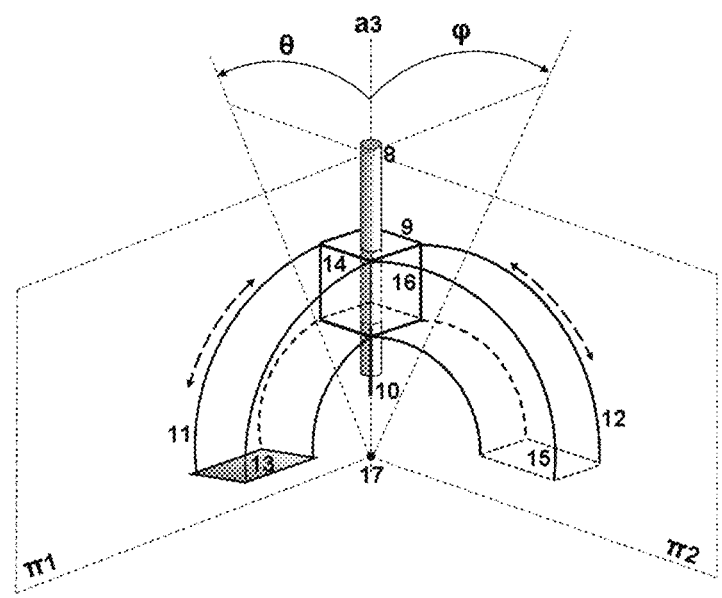
FIG. 5 shows the angular movements which the tool holder may adopt.

The orientation of the tool holder 8 is defined by two angular movements in two perpendicular planes π1 and π2, as illustrated in FIG. 5. The plane π1 is the plane perpendicular to the plane of the platform and comprising the axis a1; the plane π2 is the plane perpendicular to the plane of the platform comprising the axis a2. The axis a3 shown in FIG. 5 is the initial position (perpendicular to the platform) from which the tool holder 8 has to be oriented.

Figure 6:
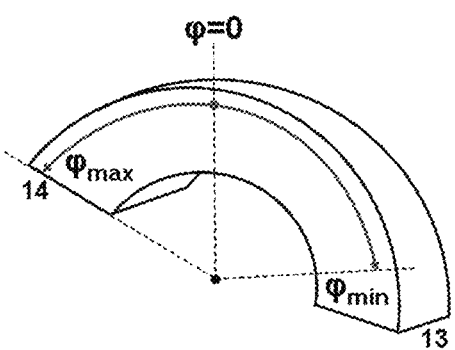
FIG. 6 illustrates the extreme positions which the tool holder may reach according to one of the degrees of freedom.

The two angular movements are therefore respectively associated with the angles φ and θ measured from the axis a3 shown in FIG. 5. From its initial position φ=0 and θ=0, the tool holder 8 may, via the antagonistic actuators, attain for each of the degrees of freedom φ or θ, a maximum position $\varphi_{max}$ or $\theta_{max}$ and a minimum position $\varphi_{min}$ or $\theta_{min}$, as this is illustrated in FIG. 6 for the angle φ and for one of the actuators 11 with the contact surfaces 13 and 14.

Figure 7:
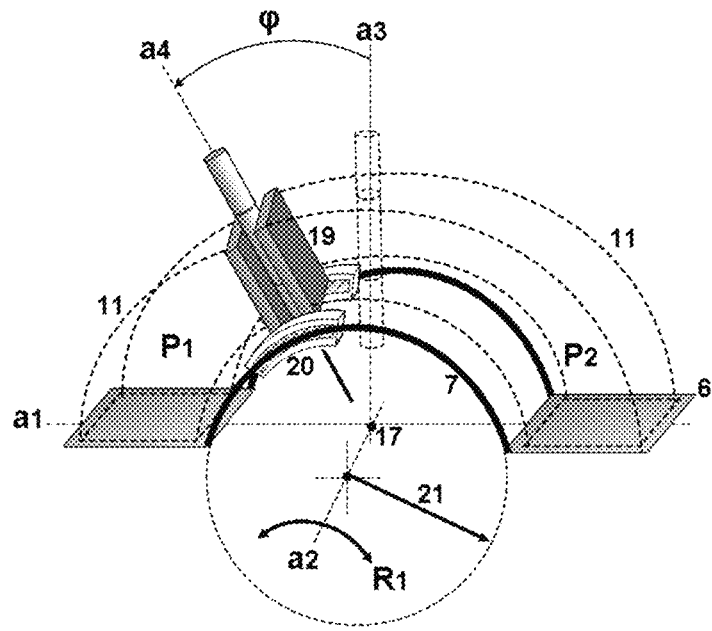
FIG. 7 illustrates the displacement according to a first degree of freedom of the tool holder under the effect of the antagonistic work of both actuators.

FIG. 7 illustrates the movement produced on the tool holder by the antagonistic work of both actuators 11 drawn in dotted lines. In the case shown, the compressed air pressure P1 of the left actuator is less than the pressure P2 of the right actuator. This pressure difference allows the followers 20 to move on the guide 7, thereby changing the angular position of the tool holder.

The generated angle φ is therefore measured between the axis a3 associated with the initial position and the axis a4 associated with the final position of the tool holder. This angular movement is defined by a rotation R1 carried out with respect to the axis a2 of FIG. 7.

It is possible to observe in this figure that the imaginary circumference with radius 21 is used for designing the guide 7 and that the axis a2 is lower than the plane of the rectangular platforms 6. Indeed, the circumference arc defining the guide 7 is designed and placed in such a way that the point 17 for inserting the needle 10 is on the lower plane of the platform 1 coinciding with the skin of the patient. The same principle of actuation is used for producing the rotation by an angle θ of the tool holder, by the antagonistic work of both actuators 12 drawn in dotted lines in FIG. 8.

Figure 8:
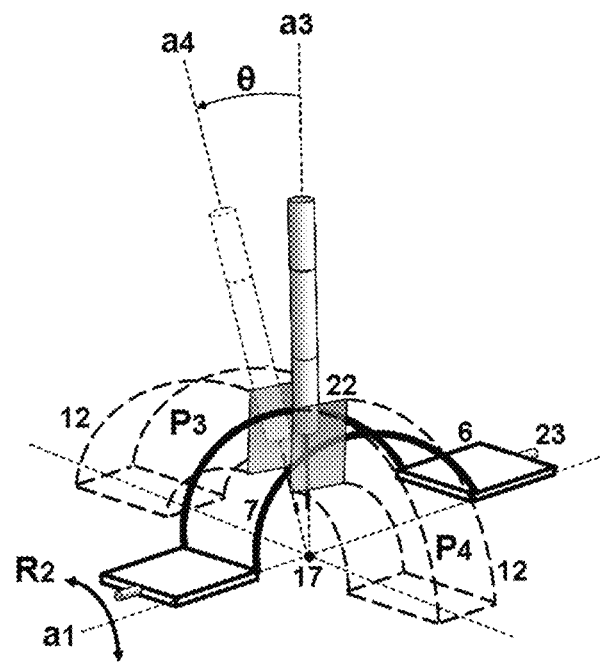
FIG. 8 illustrates the displacement according to a second degree of freedom of the tool holder resulting from the antagonistic work of two other actuators.

When the pressures P3 and P4 are equal, the position of the tool holder is the one shown in FIG. 8 by solid lines. If P4 increases by the same value by which P3 decreases, the tool holder moves by an angle θ and reaches its final position drawn in dotted lines in this figure. The tool holder turns with respect to the axis a1 defining a rotation R2.

The rigid assembly of both rectangular platforms 6 and of both circular guides 7 rotate with the tool holder by means of two plates 22 receiving both contact surfaces 16 of the actuators 12 and by means of two smooth bolts 23 ensuring their assembling with the platform 1. The generated angle θ is measured between the axis a3 associated with the initial position and the axis a4 associated with the final position of the tool holder. Because of its design, the device allows the angular position of the tool holder to be varied continuously, with great rapidity, so that the response of the system does not have practically any delay. More advantageously, the design of the tool holder is based on the same principle as the one of the positioning device, i.e. pneumatic actuation by deformable volumes in a direction determined according to their internal pressure.

The tool holder then appears as a casing, for example a cylindrical casing, inside which is laid out a piston rigidly bound to the tool and surrounded by two deformable pneumatic actuators, so that a change in pressure of at least one of the actuators causes sliding of the piston in the casing. Depending on the needs, the translation axis of the tool may coincide with that of the sliding of the piston, or else be distinct from the latter.

Figure 9:
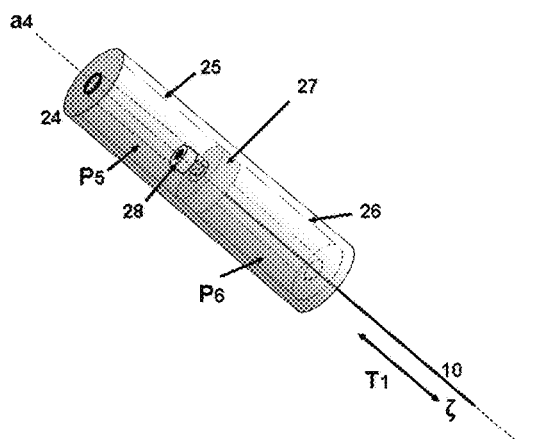
FIG. 9 illustrates a first embodiment of the tool holder.

FIG. 9 illustrates one of the possible designs of the tool holder 8. This tool holder contains the surgical tool such as needle 10 or an endoscope as well as the members guaranteeing the translation T1 of the surgical tool, following the direction ζ along the axis a4.

Inside the cylindrical casing 24 two deformable actuators 25 and 26 are found, made in flexible plastic and working antagonistically. These actuators are toroidal cylinders allowing the passage of the tool placed on the piston 27 being used as an interface between both actuators. If the tool is a needle, its upper portion 28 may be connected to another device for example a catheter.

The pressure difference between the values of P5 and P6 will cause displacement of the piston 27 and therefore of the surgical tool. The travel of the tool is in this case defined by the length of the actuators.

Figure 10:
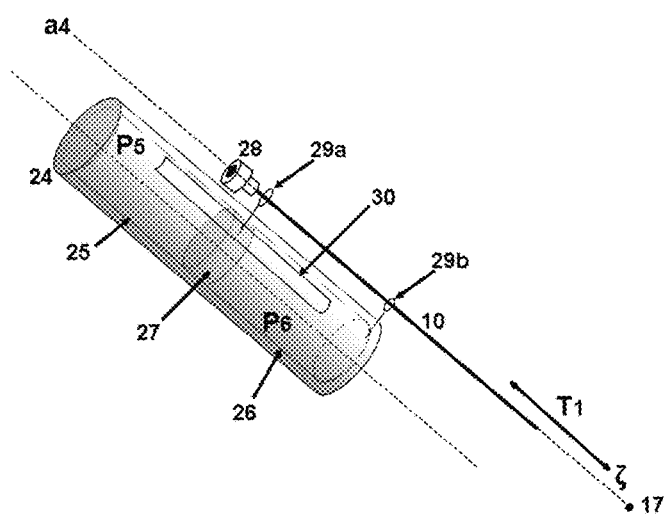
FIG. 10 illustrates a second embodiment of the tool holder.

A second possible design of the tool holder 8 is shown in FIG. 10 where the axis of the tool does not coincide with that of the tool holder but where both of these axes are parallel. In this case, the actuators 25 and 26 are simple cylinders working with the same principle as in the previous case.

The piston and the casing bear circular guides 29a and 29b with diameters generally different being used for maintaining parallelism between the axis of the tool and that of the tool holder. The guide 29a rigidly assembled to the piston 27 and to the tool 10 may move translationally inside the slot 30 made in the casing 24. The travel of the tool is in this case defined by the length of the slot 30. The guide 29b is fixed relatively to the tool holder and guides the displacement of the tool.

It is obvious that the tool holder which has just been described is fully a subject matter of the present invention. More advantageously, the whole of the components of the device (notably the platform, the orientable support, the actuators, the tool holder) may be in non-metal and non-magnetic, for example plastic, materials. Thus, the device is compatible with magnetic resonance and tomography environments.

Moreover, the thereby formed device has a particularly reduced size, since it is comprised in a tube with a side of about 10 cm, which simplifies its installation in the operating environment. It also has the advantage of being very lightweight. Thus, the mass of the prototype developed by the inventors is less than 1 kilogram.

Finally, the natural compliance of the device promotes the safety of the patient during the generation of forces capable of injuring the patient. Indeed, if the surgical tool is a needle, the deformable pneumatic actuators have sufficient flexibility for allowing the needle, when it is inside the body of the patient, to move following the movements of breathing and of the organs, which allows the risk of injuries to be reduced. On the other hand, if the system was not compliant (this would be the case with a system holding the needle rigidly, such as pneumatic actuators of the piston-cylinder type of the prior art), the movements due to breathing and to the organs would be able to cause injuries by scratching or perforating the organs. Thus, for a compliant system, when there exists a significant force acting on the system, the latter reacts following the direction of the force and does not oppose this force.

Figure 11:
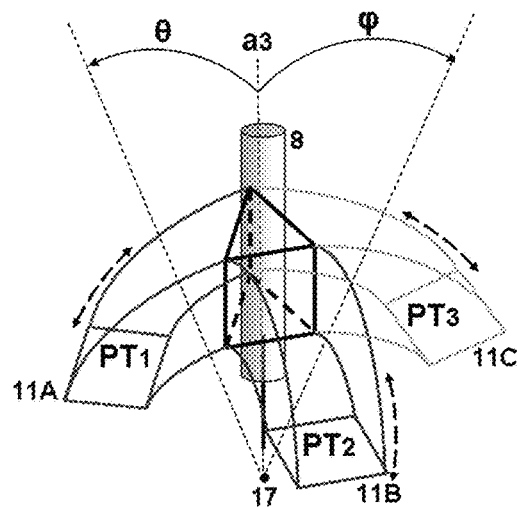
FIG. 11 illustrates an alternative embodiment of the device according to the invention.

Different configurations for the actuation with pneumatic chambers may be contemplated; in particular, concerning the geometry of the pneumatic actuators and their arrangement. FIG. 11 thereby illustrates an alternative embodiment of the invention comprising a triangular arrangement of the actuators 11A, 11B and 11C with which, depending on the three pressure values PT1, PT2, and PT3, a final position of the tool holder 8 may be obtained, associated with a combination of the values of the angles φ and θ. In this device with three actuators, the latter are placed at 120° from each other.

Figure 12:
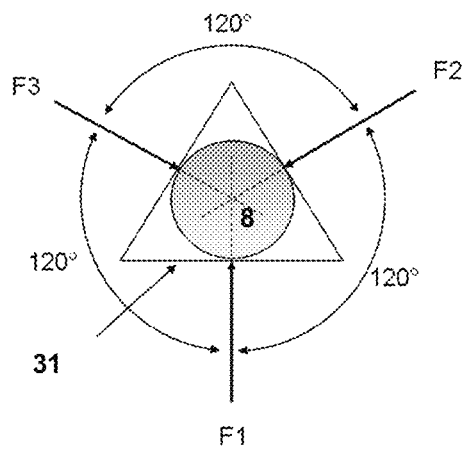
FIG. 12 shows the forces applied to the orientable support in the device of FIG. 11.

The tool holder therefore receives, through the action of three pressures on three contact surfaces, three forces (F1, F2 and F3) acting towards the axis of the tool holder, as illustrated in FIG. 12. When these forces have the same value (i.e. the resulting force is 0), the axis of the tool holder is vertical. A rotoid joint placed in proximity to the point for inserting the tool allows the tool holder to be oriented following the direction of the resulting force.

The principle of operation remains similar to the case of four actuators where contact plates are used for ensuring power transmission by means of the pneumatic pressures in each actuator. The tool holder 8 is then a sort of mast rigidly bound to an orientable support appearing as a triangular prismatic structure 31 in order to receive three contact surfaces, one for each of the three actuators.

Figure 13:
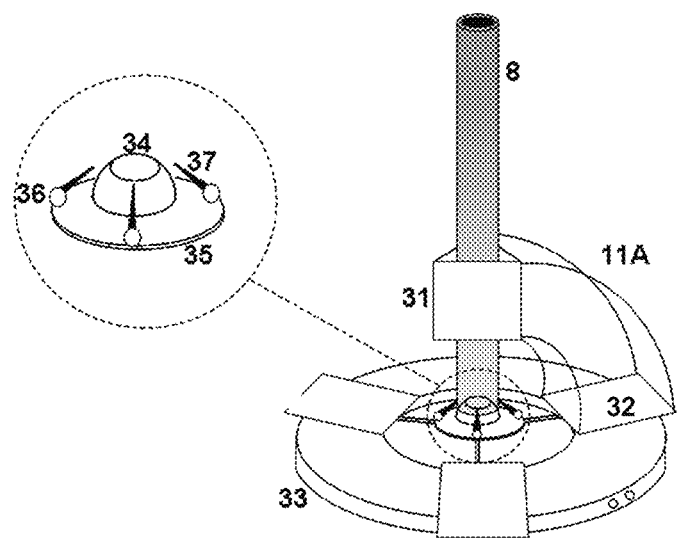
FIG. 13 illustrates in a more detailed way the construction of the design of the device of FIG. 11.

In FIG. 13, the actuator 11A may thus be observed in contact with the triangular prism 31 on the one hand and with one of the three plates 32 resting on the platform 33 similar to the platform 1 of FIG. 1, on the other hand. The tool holder remains in contact with the spherical surface 34 (which forms a large rotoid joint) by means of three telescopic mechanical members 37 which bend or extend depending on the combinations of the pressures in the three pneumatic chambers. These telescopic members 37 are attached to the tool holder 8 and to the platform 35 through passive rotoid joints 36. The platforms 33 and 35 are bound by three rigid members shown in the same figure. On the edge of the platform 33, the two holes used for receiving the fingers d shown in FIG. 3 may also be observed.

Finally, it is obvious that the examples which have just been given are only particular illustrations, by no means limiting as to the fields of application of the invention.

The invention claimed is:

1. A device for positioning and orienting in a body of a patient a surgical tool borne by a tool holder, comprising:
   a platform configured to be placed on the body of the patient;
   an orientable support, at least one portion of which is rigidly bound to the tool holder;
   a guide allowing rotation of the orientable support with respect to the platform in two directions of a plane parallel to the platform;
   at least two pneumatic actuators, each of the at least two pneumatic actuators extending between the platform and the orientable support along a curved axis, each of the at least two pneumatic actuators being shaped as a portion of a torus and cooperating with the orientable support so that a change in pressure of at least one of the at least two pneumatic actuators generates a rotation of the orientable support in at least one of the two directions, wherein angular displacement of the tool holder is rotationally guided by the orientable support such that the tool holder has an orientation defined by two angles in first and second planes that are perpendicular to one another, and wherein the first plane is perpendicular to the platform and comprises a first axis and the second plane is perpendicular to the platform and comprises a second axis;

wherein each of the at least two pneumatic actuators is a hollow and flexible casing which is deformable along the curved axis depending on internal pressure, the casing having a face firmly attached to one of: the platform and the guide, and a face firmly attached to the orientable support, so that a change in the internal pressure causes displacement of the face firmly attached to the orientable support.

2. The device according to claim 1, wherein: the at least two pneumatic actuators are four in number; the orientable support comprises two pairs of plates, both plates of each of the two pairs of plates being parallel to each other and orthogonal to plates in other pairs of plates; and the at least two pneumatic actuators are laid out in antagonistic pairs so that an internal pressure of an actuator firmly attached to a first plate of the orientable support varies in an opposite direction to an internal pressure of an actuator firmly attached to a second plate opposite the first plate.

3. The device according to claim 2, wherein the guide comprises two semi-circular guides positioned longitudinally in a first direction of the two directions and a first pair of plates of the orientable support is slideable along the two semi-circular guides.

4. The device according to claim 3, wherein the two semi-circular guides are further rotationally mobile around the first direction.

5. The device according to claim 4, wherein the two semi-circular guides are firmly attached to a second pair of plates of the orientable support.

6. The device according to claim 1, wherein the surgical tool operably translates in a direction parallel to an axis of the tool holder, the guide cooperating with deformable pneumatic actuators in a determined direction depending on internal pressure, so that a change in pressure of at least one of the pneumatic actuators generates translation of the surgical tool.

7. The device according to claim 6, wherein a translation axis of the surgical tool coincides with the axis of the tool holder and the pneumatic actuators are toroidal cylinders forming toruses, so that the surgical tool slides inside the toruses.

8. The device according to claim 7, wherein the translation axis of the surgical tool is distinct from the axis of the tool holder and the pneumatic actuators are cylinders.

9. The device according to claim 1, wherein the at least two pneumatic actuators are three in number and the orientable support is a prism with a triangular base having three side faces, so that each of the at least two pneumatic actuators is firmly attached to one of the three side faces of the orientable support.

10. The device according to claim 1, further comprising an arm of a surgical aid robot that is connected to the platform by at least one passive rotoid joint.

11. The device according to claim 1, wherein the platform, the orientable support, the at least two pneumatic actuators and the guide are non-metal and non-magnetic materials, so that the device is capable of use in at least one of: tomography and magnetic resonance.

12. A tool holder adapted so as to be used in the device according to claim 1, further comprising a piston rigidly bound to the surgical tool, slidably mobile in a casing along a longitudinal direction parallel to the axis, two pneumatic actuators located in the casing on either side of the piston, deformable in a determined direction depending on internal pressure, and cooperating with the piston so that a change in pressure in at least one of the pneumatic actuators generates sliding of the piston along the determined direction.

13. The tool holder according to claim 12, wherein a translation axis of the surgical tool and a sliding direction of the piston coincide and wherein the pneumatic actuators are toroidal cylinders, the inner diameter of which is larger than the diameter of the surgical tool.

14. The tool holder according to claim 12, wherein a translation axis of the surgical tool and a sliding direction of the piston are distinct and wherein the casing has a longitudinal slot for sliding a member connecting the piston and the surgical tool.

15. A device for positioning and orienting in the body of a patient a surgical tool borne by a tool holder, comprising:
a first patient-contacting platform that extends along a first plane and defines a cavity therein, the cavity receiving the surgical tool when the surgical tool is deployed from the tool holder;
an orientable support spaced from the first patient-contacting platform that receives the surgical tool and the tool holder;
a second platform pivotally mounted on the first patient-contacting platform for translation relative to the first plane about a first axis that extends along the first plane;
at least one guide connected to the second platform that extends over the cavity of the first patient-contacting platform, the orientable support being slideably supported on the at least one guide for translation relative to the first plane about a second axis that extends along the first plane and intersects the first axis; and
pneumatic actuators operably moving the orientable support, and external casings of the pneumatic actuators being partially circular in length and flexible;
each of the pneumatic actuators being shaped as a portion of a torus and cooperating with the orientable support so that a change in pressure of at least one of the pneumatic actuators generates a rotation of the orientable support in at least one direction, wherein angular displacement of the tool holder is rotationally guided by the orientable support such that the tool holder has an orientation defined by two angles in two planes that are perpendicular to one another and are perpendicular to the first patient-contacting platform.

16. The device of claim 15, further comprising:
a first of the pneumatic actuators being coupled to the first patient-contacting platform and the orientable support that rotates the orientable support about the first axis by pivoting the second platform with respect to the first patient-contacting platform in response to actuation of the first pneumatic actuator; and
a second of the pneumatic actuators being coupled to the second platform and the orientable support that rotates the orientable support about the second axis by sliding the orientable support along the at least one guide in response to actuation of the second pneumatic actuator.

17. The device of claim 16, wherein the external casings of the first and second pneumatic actuators are entirely hollow and deformable due to internal pneumatic pressure.

18. The device of claim 16, wherein the first pneumatic actuator extends in a partial torus shape between the first patient-contacting platform and the orientable support and the second pneumatic actuator extends in a partial torus shape between the second platform and the orientable support.

19. The device of claim 16, wherein the first and second axes are perpendicular and the first pneumatic actuator is coupled to the first patient-contacting platform along the second axis and the second pneumatic actuator is coupled to the second platform along the first axis.

20. A device for positioning and orienting in a body of a patient a surgical tool borne by a tool holder, comprising:
- a platform adapted for placement on the body of the patient;
- an orientable support, at least one portion of which is connected to the tool holder, comprising pairs of plates, plates in each pair of plates being parallel to each other and orthogonal to plates in other pairs of plates;
- semi-circular guides positioned longitudinally in a first direction and rotationally mobile around the first direction, plates being slideable along the semi-circular guides so as to guide in rotation the orientable support with respect to the platform in two directions of a plane parallel to the platform; and
- four pneumatic actuators, each of the pneumatic actuators being shaped as a portion of a torus and cooperating with the orientable support so that a change in pressure of at least one of the pneumatic actuators generates a rotation of the orientable support in at least one of the two directions, wherein angular displacement of the tool holder is rotationally guided by the orientable support such that the tool holder has an orientation defined by two angles in first and second planes that are perpendicular to one another, and wherein the first plane is perpendicular to the platform and comprises a first axis and the second plane is perpendicular to the platform and comprises a second axis;

wherein the pneumatic actuators are deformable depending on the internal pressure and casings of the pneumatic actuators are flexible plastic, each having a face firmly attached to at least one of: the platform and the guides, and a face firmly attached to the orientable support, so that a change in the internal pressure causes displacement of the face firmly attached to the orientable support, and wherein the pneumatic actuators are laid out in antagonistic pairs on both sides of the orientable support so that the internal pressure of an actuator firmly attached to a first of the plates of the orientable support varies in the opposite direction to the internal pressure of the actuator firmly attached to a second of the plates opposite the first of the plates.

* * * * *